United States Patent [19]

Shah et al.

[11] Patent Number: 4,486,412
[45] Date of Patent: Dec. 4, 1984

[54] ENCAPSULATED ANTACID DISPERSIONS

[75] Inventors: Dilip Shah, Parsippany; Lionel Borkan, New Vernon; Ira R. Berry, Westfield, all of N.J.

[73] Assignee: Pharmacaps, Inc., Elizabeth, N.J.

[21] Appl. No.: 475,491

[22] Filed: Mar. 15, 1983

[51] Int. Cl.$^3$ .................... A61K 33/10; A61K 33/08; A61K 33/06; A61K 33/42

[52] U.S. Cl. ................................... 424/156; 424/157; 424/128; 424/127; 424/154; 424/319; 424/31

[58] Field of Search .................. 424/31, 38, 128, 157, 424/158, 156, 154, 127, 319

[56] References Cited

U.S. PATENT DOCUMENTS

| | | | |
|---|---|---|---|
| 3,767,794 | 10/1973 | McVean et al. | 424/156 |
| 3,843,778 | 10/1974 | Diamond et al. | 424/38 |
| 4,002,718 | 1/1977 | Gardella et al. | 424/37 |
| 4,067,960 | 1/1978 | Fadda | 424/14 |
| 4,088,750 | 5/1978 | Cresswell et al. | 424/37 |
| 4,150,110 | 4/1979 | Yoshida et al. | 424/33 |
| 4,198,391 | 4/1980 | Grainger | 424/37 |

OTHER PUBLICATIONS

*Handbook of Nonprescription Drugs,* Fifth Ed., 1977, American Pharmaceutical Association, Wash., D.C., pp. 13 & 17.

*Primary Examiner*—Frederick E. Waddell

[57] ABSTRACT

Pharmaceutical unit dosage forms comprising dispersions of basic salts in a carrier mixture comprising polyalkylene glycols and a $C_2$–$C_5$ polyol encapsulated in soft gelatin capsules are prepared without deleteriously affecting the stability of the capsules.

25 Claims, No Drawings

ENCAPSULATED ANTACID DISPERSIONS

BACKGROUND OF THE INVENTION

Soft gelatin encapsulation of a solution or dispersion of a pharmaceutical agent in a liquid carrier offers many advantages over other dosage forms such as compressed, coated or uncoated solid tablets or bulk liquid preparations. Gelatin encapsulation of a solution or dispersion permits accurate delivery of a unit dose, an advantage which becomes especially important when relatively small amounts of the active ingredient must be delivered, as in the case of certain hormones. Such uniformity is more difficult to achieve via a tabletting process wherein solids must be uniformly mixed and compressed, or via incorporation of the total dose of active ingredient into a bulk liquid carrier which must be measured out prior to each oral administration.

Soft gelatin encapsulation provides a dosage form which is more readily accepted by patients, since the capsules are easy to swallow and need not be flavored in order to mask the unpleasant taste of the active principle. Soft gelatin capsules are also more easily transported by patients than bulk liquids, since only the required number of doses need be removed from the package.

Soft gelatin encapsulation further provides the potential to improve the bioavilability of pharmaceutical agents. Active ingredients are rapidly released in liquid form as soon as the gelatin shell ruptures. Complete disintegration and dissolution of the capsule are not necessary for the active ingredients to become available for absorption as in the case of tabletted compositions. Also, relatively insoluble active ingredients can be dispersed in a liquid carrier to provide faster absorption. In the case of an oral liquid preparation, a significant amount of the active ingredient is lost in the mouth or esophageal lining, prior to absorption into the blood.

Currently available antacid preparations are designed for the symptomatic relief of heartburn (pyrosis), sour stomach, indigestion, gas and the hyperacidity associated with peptic ulcer, gastritis, gastric hyperactivity and hiatal hernia. These preparations contain one or more basic magnesium, aluminum or calcium salts which act to neutralize stomach acid. For example, Maalox ® Plus (W. H. Rorer, Inc., Ft. Washington, Pa.) is available as a liquid which is formulated to deliver 200 mg of magnesium hydroxide, 225 mg of aluminum hydroxide and 15 mg. of simethicone, a gas dispersing agent, per dose. The tablet form of this product is similar except that it contains 200 mg of aluminum hydroxide per dose. Tums ® (Norcliff Thayer, Inc., Tuckahoe, NY) contains about 500 mg of calcium carbonate per tablet. Other commercially available antacid compositions contain varying amounts of magnesium silicate, magnesium carbonate, bismuth aluminate, magnesium oxide, dihydroxy aluminum sodium carbonate, magaldrate and similar basic salts.

The advantages which would be attained by delivering these salts as dispersions or solutions via soft gelatin encapsulation have been enumerated hereinabove. However, delivery of such formulations in this manner has not heretofore been possible due to the chemical destabilization of gelatin, i.e. of type A or B, in the presence of strongly alkaline salts, leading to the leaking or bleeding of the capsule contents at elevated pH. Further, the edible oils which have traditionally been used as carriers for pharmaceuticals in soft gelatin capsules effectively reduce the neutralizing capacity of the antacid components.

It is therefore an object of the present invention to provide liquid dispersions of basic salts which are suitable for, and compatable with, soft gelatin encapsulation.

It is another object of the present invention to provide dispersions of basic salts, e.g., calcium, magnesium and aluminum salts, which are adapted for oral, vaginal, rectal or buccal administration when contained within soft gelatin capsules.

It is another object of the present invention to provide dispersions of basic salts in carriers which do not adversely effect the neutralizing capacity of the basic salts.

Other objects, advantages and novel features of the present invention will be apparent to those of skill in the art from the following description and appended claims.

BRIEF DESCRIPTION OF THE INVENTION

The objects of the present invention are attained by a pharmaceutical unit dosage form comprising a dispersion of a basic salt or salts in a substantially water-free carrier mixture comprising one or more polyalkylene glycols and a $C_2$–$C_5$ polyol such as glycerin or proplyene glycol. The mixture of alcohols acts to form a stable dispersion of the particles of the basic salt which are coated by the carrier mixture and rendered substantially non-reactive with the soft gelatin capsules in which the dispersion is subsequently enclosed. Optional amounts of plasticizers and base-compatible pharmaceutical agents may also be incorporated in the dispersions of the present invention.

As used herein, the term "substantially water-free" is defined to mean that water present in the starting materials as provided by the manufacturers or as acquired by hygroscopic attraction may be present in the carrier mixture, as well as minor amounts of added water which are insufficient to deleteriously effect the capsule wall stability.

DETAILED DESCRIPTION OF THE INVENTION

The compositions of the present invention permit the encapsulation, storage and delivery via soft gelatin encapsulation of basic salts which would normally be chemically-incompatible with soft gelatin if formulated in a dispersion or solution in a pharmaceutically or cosmetically effective amount. To overcome this incompatibility, the basic salt is dispered in a substantially water-free carrier comprising a mixture of a polyalkylene glycol and a $C_2$–$C_5$ polyol, e.g. propylene glycol or glycerin. The carrier mixture is formulated so as to form a stable dispersion of the basic salt and to coat the salt particles so as to render them substantially non-reactive with soft gelatin. When encapsulated in flexible, soft gelatin capsules, the dispersed salts do not cause leakage or bleeding of the dispersions through the capsule walls.

The basic salts and other compatible active agents then remain available for oral, rectal, vaginal, buccal or topical administration. The basic salts which are dispersed, encapsulated and delivered via the compositions of the present invention are any of those inorganic or organic metal salts which may be incompatible with soft gelatin, including the salts of magnesium, aluminum, sodium, calcium, bismuth, zinc, zirconium and titanium.

The dispersions of the present invention are particularly suited for the delivery of effective amounts of the commonly-used orally-administered antacid salts. These salts include aluminum, magnesium, sodium and calcium salts such as magnesium hydroxide, sodium bicarbonate, aluminum hydroxide, magnesium oxide, magnesium carbonate, calcium carbonate, magnesium silicate, dihydroxy aluminum sodium carbonate, magaldrate, dihydroxy aluminum aminoacetate, magnesium phosphate and mixtures thereof. Preferred antacid salts include magnesium hydroxide, aluminum hydroxide, calcium carbonate and mixtures thereof, due to their high neutralizing power and absence of significant side effects. It will be appreciated from the foregoing that the term "basic salt" as used herein includes effective hydroxides and salts as well as compounds traditionally referred to as basic salts.

The amount of the basic salt or salts incorporated into the antacid dispersions will vary depending on the neutralizing power desired to be delivered per unit dosage form (e.g., via one capsule containing up to about 1500 mg of dispersion. The amount of encapsulated dispersion will include sufficient basic salt to neutralize at least about 5 mEq of hydrochloric acid, preferably from about 5 to about 30 mEq of aqueous hydrochloric acid and most preferably from about 5 to about 20 mEq.

Other gastrointestinal agents which are compatible with the basic salt may be included in the dispersions of the present invention. These include the polysiloxane flatulence-relieving agents such as simethicone, which act to relieve symptoms resulting from the retention of excessive gas. Such optional agents will typically comprise about 0-5% by weight of the total dispersion.

The dispersions of the present invention also permit the soft gelatin encapsulation of basic salts such as those employed in cosmetic or pharmaceutical formulations adapted to deodorize, moisturize, protect or heal skin via topical application. Such salts include the hydroxides, oxides and carbonates of zinc, magnesium, aluminum, zirconium or titanium.

The amount of the basic salt or salts employed as a weight percent of the total dispersion may vary widely depending upon its biological activity and intended use, i.e., from about 5-70%, preferably from about 20-60%.

The liquid carrier mixture employed to disperse the basic salts comprises a substantially water-free mixture of a major proportion of one or more polyalkylene glycols and a minor proportion of a $C_2$–$C_4$ diol or triol, preferably propylene glycol.

The polyalkylene glycol component may comprise a polyethylene glycol, a polypropylene glycol or a mixed polyethylene/polypropylene glycol having a molecular weight within the range of about 100-9000. Preferably the polyalkylene glycol component will comprise a mixture of a major proportion of a liquid polyethylene glycol, i.e., polyethylene glycol-200, 300, 400 or 600 wherein the suffixed numbers indicate the approximate molecular weight of the glycol; and a minor proportion of a waxy polyethylene glycol having a molecular weight in the range of about 800-9000, i.e., polyethylene glycol-900, 1000, 1450, 1500, 3350, 3400, 4500 or 8000. Preferably the ratio of liquid to waxy polyethylene glycol will be about 15-40:1, most preferably about 20-35:1. Preferably, the polyalkylene glycol will comprise about 20-80% by weight of the entire dispersion, most preferably about 30-70% by weight.

The carrier mixture of the present invention will also comprise a minor but effective amount of a $C_2$–$C_4$ polyol, e.g. a diol or triol such as propylene glycol or glycerin, which acts to adjust the viscosity of the dispersion and to stabilize the dispersion. A preferred polyol is propylene glycol, which will preferably comprise 0.2-10% by weight of the present dispersions, most preferably 1.0-3.0% by weight.

The dispersions of the present invention may optionally comprise minor but effective amounts of one or more nonionic surfactants such as the $C_{12}$–$C_{20}$ fatty acid esters of sorbitol and its anhydrides ("Spans") optionally copolymerized with about 15-90 moles of ethylene oxide ("Tweens"). Typical polysorbates which aid in the formation of the present dispersions and help to stabilize the gelatin capsule include polysorbate 20 (a laurate ester); polysorbate 40 (a palmitate ester); polysorbate 60 (a mixture of stearate and palmitate esters); and polysorbate 80 (an oleate ester) wherein the suffixed numbers indicate the approximate mole ratio of ethylene oxide to sorbitol. The polysorbates may be present in an amount from about 0-5% by weight of the dispersion. For a general discussion of the properties and composition of the polyethylene glycols and the polysorbates, see Remington's Pharmaceutical Sciences, A. Osol, ed., Mack Pub. Co. (16th ed. 1980) at pages 1252-1253, the disclosure of which is incorporated by reference herein.

Therefore, preferred antacid dispersions formulated in accord with the present invention will comprise an amount of basic aluminum, magnesium, or calcium salt adequate to neutralize about 5-25 mEq. of hydrochloric acid per unit dose; about 30-50% of a mixture of a waxy and a liquid polyethylene glycol; about 0.2-10% of propylene glycol, about 0-5% of a polysorbate, and about 0-5% of a gas-dispersing flatulence-relieving agent.

The dispersions of the present invention are generally prepared by heating and mixing together the polyalkylene glycols, followed by the room temperature addition of a mixture of the active ingredients, propylene glycol and, optionally, the polysorbates. The resultant dispersion is then milled, deaerated, and filled into gelatin capsules of a suitable unit dose size via a rotary die encapsulation machine or similar encapsulating device.

The invention will be further described by reference to the following detailed examples.

EXAMPLE I - HYDROXIDE DISPERSION

Polyethylene glycol-3350 (182 kg) was dissolved in 5586 kg of polyethylene glycol-400 with stirring at 60° C. The solution was then cooled to 30° C. A mixture of 1400 kg magnesium hydroxide, 1575 kg of aluminum hydroxide (dried aluminum hydroxide gel—77%) 175 kg of simethicone, 182 kg of propylene glycol and 140 kg of polysorbate 80 was stirred into the glycol solution over 60 minutes. The dispersion was Fitz milled to reduce any remaining particle aggregates, vacuum-deaerated and filled into oblong soft gelatin (#20) capsules at a dose of 1320 mg per capsule. The dispersion batch resulted in about $7 \times 10^6$ filled capsules.

The amount of dispersion encapsulated (1320 mg) neutralized 10.7 mEq. of hydrochloric acid when titrated according to standard methods and gave a preliminary antacid test reading of pH 7.2 (C.F.R. Title 21, Ch. 1, §§331.26 and 331.25). Under a standard antacid disintegration test, the filled capsule ruptured in 4.5 minutes and the shell completely dissolved in 9 min. (C.F.R. Title 21, Ch. 1, §331.24). These results demonstrate a per unit acid neutralizing capacity and antacid availability which are equivalent or superior to Maalox ® Plus tablets.

EXAMPLE II - CARBONATE DISPERSION

Polyethylene glycol-3350 (140 kg) was dissolved in a 60° C., stirred portion of polyethylene glycol-400 (3220 kg). The solution was cooled to 30° C. and 3500 kg of calcium carbonate added with mechanical stirring over 1 hr. The mixture was passed through a Fitz Mill, vacuum deaerated and 1000 mg filled into each of $7 \times 10^6$ soft gelatin capsules (#14) by means of a rotary die encapsulation machine.

One filled capsule neutralized 10.0 mEq of hydrochloric acid, gave a preliminary antacid test reading of pH 6.4, ruptured within 3.5 minutes and the shell dissolved within 7.0 minutes when tested by the procedures of Example I. These results demonstrate a per unit dose acid neutralizing capacity and antacid availability which are equivalent or superior to Tums ® tablets.

Preliminary stability testing of filled capsules prepared according to Exs. I or II indicate a projected shelf-life of 2-3 years at ambient temperatures and humidities. Therefore, examples I and II demonstrate the preparation of potent encapsulated antacid dispersions which are quickly released from the capsules in an aqueous acidic environment but which do not negatively affect capsule wall stability upon storage.

It is expected that dispersions formulated according to the present invention will permit the soft-gelatin encapsulation and administration of a wide variety of basic salts useful for pharmaceutical, dietary or cosmetic applications.

While certain representative embodiments of the invention have been described herein for purposes of illustration, it will be apparent to those skilled in the art that modifications therein may be made without departing from the spirit and scope of the invention.

We claim:

1. A pharmaceutical unit dosage form comprising a soft gelatin capsule containing a dispersion of particles of a pharmaceutically-effective amount of a basic salt in a substantially water-free liquid carrier comprising a mixture of polyalkylene glycol and a $C_2$-$C_5$ polyol; said carrier being present in an amount effective to coat the particles of the salt and thereby render them substantially non-reactive with said gelatin capsule.

2. The unit dosage form of claim 1 wherein the basic salt is selected from the group consisting of aluminum, magnesium, sodium and calcium salts.

3. The unit dosage form of claim 2 wherein the basic salt is selected from the group consisting of magnesium phosphate, magnesium hydroxide, magnesium oxide, magnesium carbonate, aluminum hydroxide, dihydroxy aluminum sodium carbonate, magaldrate, dihydroxy aluminum aminoacetate, sodium bicarbonate, calcium carbonate and mixtures thereof.

4. The unit dosage form of claim 1 wherein the polyalkylene glycol comprises a polyethylene gylcol and wherein the polyol comprises propylene glycol.

5. The unit dosage form of claim 4 wherein the polyalkylene glycol comprises a mixture of a liquid polyethylene glycol and a waxy polyethylene glycol.

6. The unit dosage form of claim 5 wherein the polyalkylene glycol comrpsies a mixture of polyethylene glycol 400 and polyethylene glycol 3350 in a weight ratio of about 15-40:1.

7. The unit dosage form of claim 3 wherein the dispersion comprises about 20-60% by weight of the basic salt, about 20-80% polyethylene glycol and about 0.2-10% propylene glycol.

8. The unit dosage form of claim 7 wherein the dispersion further comprises an effective amount of no more than about 5% by weight of polysorbate.

9. The unit dosage form of claim 8 wherein the basic salt is a mixture of aluminum hydroxide and magnesium hydroxide, the polyethylene glycol is a mixture of polyethylene glycol 400 and polyethylene glycol 3350 and the polysorbate is polysorbate 80.

10. The unit dosage form of claim 9 further comprising an effective flatulence-relieving amount of simethicone.

11. The unit dosage form of claim 7 wherein the basic salt is calcium carbonate and the polyethylene glycol is a mixture of polyethylene glycol 400 and polyethylene glycol 3350.

12. The unit dosage form of claim 6 wherein the basic salt is selected from the group consisting of calcium carbonate, magnesium hydroxide, aluminum hydroxide and mixtures thereof.

13. A method for alleviating the symptoms of excessive gastic acidity comprising orally administering a soft gelatin capsule containing a dispersion comprising an amount of a pharmaceutically-effective amount of an antacid basic salt sufficient to neutralize at least about 5 mEq of hydrochloric acid and a substantially water-free liquid carrier comprising a mixture of polyalkylene glycol and a $C_2$-$C_5$ polyol effective to substantially inhibit degradation of the gelatin capsule by the basic salt.

14. The method of claim 13 wherein the polyol comprises propylene glycol.

15. The method of claim 14 wherein the basic salt is selected from the group consisting of the salts of magnesium, calcium, sodium, aluminum and mixtures thereof and is present in an amount sufficient to neutralize about 5-25 mEq of hydrochloric acid.

16. The method of claim 14 wherein the polyalkylene glycol is a mixture of a liquid polyethylene glycol having a molecular weight in the range of about 100-700 and a waxy polyethylene glycol having a molecular weight in the range of about 800-9000.

17. The method of claim 16 wherein the weight ratio of liquid polyethylene glycol to waxy polyethylene glycol is about 20-35:1.

18. The method claim 15 wherein the basic salt is selected from the group consisting of magnesium hydroxide, aluminum hydroxide, calcium carbonate and mixtures thereof.

19. The method of claim 18 wherein the basic salt comprises calcium carbonate and the polyalkylene glycol comprises about 20-80% by weight of the dispersion of a mixture of polyethylene glycol 400 and polyethylene glycol 3350 in a ratio of about 15-40:1, respectively.

20. The method of claim 18 wherein the basic salt comprises a mixture of aluminum hydroxide and magnesium hydroxide and the polyalkylene glycol comprises about 20-80% by weight of the dispersion of a mixture of polyethylene glycol 400 and polyethylene glycol 3350 in a weight ratio of about 20-35:1, respectively.

21. The method of claim 19 wherein the propylene glycol comprises about 0.2-10% by weight of the dispersion.

22. The method of claim 20 wherein the propylene glycol comprises about 0.2-10% by weight of the dispersion.

23. The method of claim 20 wherein the dispersion further comprises an effective amount of no more than about 5% by weight of polysorbate.

24. The method of claim 19 wherein the dispersion further comprises an effective amount of no more than about 5% of simethicone.

25. A method of administering a pharmaceutically-effective amount of a basic salt to a patient comprising the oral, buccal, rectal or vaginal administration of the unit dosage form of claim 1.

* * * * *